United States Patent [19]

Smoot et al.

[11] Patent Number: 4,689,255
[45] Date of Patent: Aug. 25, 1987

[54] MAT STRUCTURE

[75] Inventors: Michael A. Smoot, Oakmont; Herbert W. Barch, Natrona Heights; Balbhadra Das, Allison Park, all of Pa.

[73] Assignee: PPG Industries, Inc., Pittsburgh, Pa.

[21] Appl. No.: 916,688

[22] Filed: Oct. 8, 1986

Related U.S. Application Data

[63] Continuation-in-part of Ser. No. 636,755, Aug. 1, 1984, abandoned.

[51] Int. Cl.⁴ .................. B01D 13/01; B01D 25/06; B01D 39/00; C02F 1/44
[52] U.S. Cl. ........................................ 428/77; 55/16; 55/158; 55/527; 210/321.1; 210/321.2; 210/321.3; 210/433.2; 210/500.23; 210/500.26; 428/195; 428/210; 428/288; 428/294; 428/311.5; 428/316.6; 428/317.3
[58] Field of Search ............. 210/321.1, 321.2, 321.3, 210/433.2, 500.2, 500.23, 500.26; 55/16, 158, 527; 428/77, 195, 210, 288, 294, 311.5, 316.6, 317.3

[56] References Cited

U.S. PATENT DOCUMENTS

| | | |
|---|---|---|
| 2,106,744 | 2/1938 | Hood et al. . |
| 2,197,805 | 4/1940 | Lovett .................. 210/500.26 |
| 2,334,961 | 11/1943 | Schoenlaub . |
| 2,571,074 | 10/1951 | Tiede et al. . |
| 3,268,313 | 8/1966 | Burgman et al. . |
| 3,510,393 | 5/1970 | Burgman et al. . |
| 3,630,700 | 12/1971 | Hammel . |
| 3,650,721 | 3/1972 | Hammel et al. . |
| 3,847,626 | 11/1974 | Erickson et al. . |
| 4,042,359 | 8/1977 | Schnabel et al. . |
| 4,166,747 | 9/1979 | Neely, Jr. . |
| 4,172,794 | 10/1979 | Sigdell . |
| 4,610,789 | 9/1986 | Barch ................. 210/500.26 |

OTHER PUBLICATIONS

"Microporous Glass for Reverse Osmosis", by P. W. McMillan et al., Dept. of Physics, Univ. of Warwick Coventry, UK, pp. 1187-1199.

Primary Examiner—James C. Cannon
Attorney, Agent, or Firm—John E. Curley

[57] ABSTRACT

A novel mat composite is shown in which a plurality of glass fibers, strands or rovings are carried on a fluid permeable sheet with two generally parallel ribbons of mastic on each side of the sheet inboard of the edges affixing the fibers, strands or rovings to the sheet and maintaining the fibers, strands and rovings generally parallel to each other.

24 Claims, 4 Drawing Figures

MAT STRUCTURE

BACKGROUND OF THE INVENTION

This application is a continuation-in-part of Ser. No. 636,755, filed Aug. 1, 1984, and now abandoned.

In many filtration processes today membranes are utilized to filter various components of fluid systems. For example, membranes are used to separate gas components from each other in gaseous streams containing multiple gases, to separate various dissolved components in liquid solutions from each other and to selectively permit certain ions in a solution to pass across a membrane while blocking others. Membranes are also utilized to a great extent to immobilize proteins, enzymes and cells. The enzymes, so immobilized are used as catalysts to increase reaction rates or to convert materials in solution from one form to another. Membranes are also utilized in various applications today to trap or immobilize living cells within a substrate forming the membrane.

In general, membranes of various types have been employed for these purposes. In the electrolysis field, for example, polymer sheet membranes which are selectively permeable to alkali metal ions are utilized. Porous glass beads have also been employed in many processes for the purpose of immobilizing enzymes for use in other chemical processes. Organic fibers have also been utilized in many applications, for example, the dialysis of blood. These organic fibers have been utilized both in the hollow and porous state where the material to be purified, in this case blood, is passed through a hollow organic fiber and is purified by enriching it in oxygen and depleting it of waste materials through the pores.

Inorganic materials are particularly interesting for membrane applications since they are, generally speaking, inert and depending on composition, alkali or acid resistant. These properties render such inorganic materials useful in purification systems that are acidic or alkaline. Further, their inertness renders such inorganic materials useful in cell, protein and enzyme immobilization since they are non-reactive to these substances and also to contaminants such as microorganisms that might be present in solutions being treated. Inorganic substances further can be readily cleaned without suffering severe damage during cleaning and sterilization, whereas many organic substances cannot be cleaned using normal cleaning materials such as calcium hypochlorite solutions. Interest in inorganic substrates in the form of hollow glasses which are porous is demonstrated by an article in "The Journal of Material Science" (11), 1976 at pages 1187–1199 by P. W. McMillan and C. E. Matthews. The recent U.S. Pat. No. 4,042,359 also shows a device made of porous glass tubes. These devices use individual tubes in what appears to be limited capacity reactors since the tubes are separated from each other with each tube restrained at each end. A need, therefore, exists for inorganic substrates that can be effectively utilized in reverse osmosis, microfiltration, ultrafiltration, enzyme, protein and cell immobilization and other like processes in a commercial reactor to provide a large number of porous glass fibers for use in the process being conducted.

Applicants, by virtue of the instant invention, have supplied that need by providing the art with novel and useful mats utilizing as major components thereof glass fibers in the form of glass fiber strands and glass fiber rovings. As used herein in the specification and claims, strands means a group of a multiplicity of individual fibers gathered into a unitary bundle. As used herein in the specification and claims, rovings means a group of strands gathered together to form a unitary bundle. The glass fibers used to produce the mats whether they are used in strands or rovings, are porous glass fibers, hollow glass fibers or hollow and porous glass fibers or combinations thereof.

The mats made from these glass fiber strands and rovings may be utilized in forming cartridges for use in filtration apparatuses for gas and/or liquid separations, for reverse osmosis and ultrafiltration systems, as a carrier for cell cultures in reactors requiring large flat surface areas for cell growth, as elements in systems designed for the immobilization of proteins and enzymes, as blood dialysis membranes and other such systems. The number of fibers contained in the multiple strands and/or rovings used to prepare the mats provide hundreds of thousands to millions of individual glass fibers in a form readily adaptable for use in various filtration and immobilization reactors.

Thus, the mats of the instant invention provide in convenient form, large quantities of glass fibers, which by chemical composition, can be tailored to various media to which they may be exposed to render them resistant to reactant attack in a given process. They may also be varied in the pore sizes used when the fibers used in the strands or rovings are porous, to provide specific mats for use in ultrafiltration; reverse osmosis and the like. The diameter of the fibers used in the formation of the strands and rovings used to prepare the mats of the instant invention can be tailored to provide, in the case of hollow fibers for example, an internal lumen of a specified or given size with or without the fibers also being porous, thereby rendering mats made from such fibers useful as cell culture reactors as well as in dialysis systems.

SUMMARY OF THE INVENTION

In accordance with one embodiment of the invention, a novel mat composite is provided in which a plurality of porous glass fibers in the form of strands or rovings are carried on a generally flat, fluid permeable sheet. The strands or rovings are generally several layers in depth and are aligned on the surface of the permeable sheet substantially parallel to each other. Strips or ribbons of an adhesive are provided between the ends of the strands or rovings on the permeable sheet. The adhering ribbon is of a depth sufficient to bind the layers of the strands and/or rovings to each other and to the surface of the fluid permeable sheet. The ribbons of adhesive bind the layers of strands and/or rovings to the sheet thus forming an integral composite mat containing porous glass fibers, hollow glass fibers, or hollow and porous glass fibers in extremely large numbers covering the surface area of the mat.

In another embodiment of the invention, a second fluid permeable sheet is placed over the fibers, strands or rovings and is of a length and width sufficient to cover the first several rows of strands or rovings attached to the first permeable membrane.

The various embodiments of the inventions will be apparent to one having ordinary skill in the art from consideration of the ensuing description and claims.

BRIEF DESCRIPTION OF THE DRAWINGS

For a more complete understanding of the instant invention, reference is made to the accompanying drawings in which.

DETAILED DESCRIPTION OF THE DRAWINGS

Figure 1:
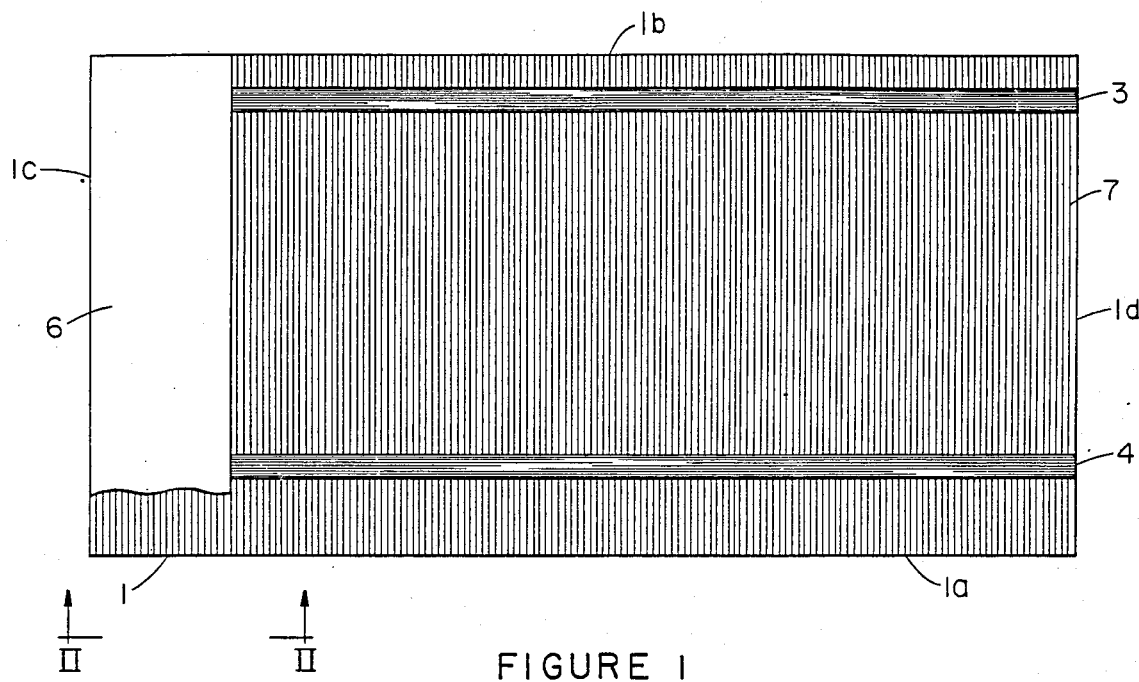
FIG. 1 is a plan view of the mat structure of the instant invention.

Turning now to the drawings and to FIG. 1 and FIG. 2 in particular, the invention will be described as it applies to an embodiment in which strands of glass fibers are used to form the mat of the invention. It will be understood that the fibers used in the strands are made of glass. While in this embodiment, the fibers are hollow, they can be porous only or porous and hollow or a combination of these forms or two of the three forms and still fall within the scope of the invention. Similarly, while strands of hollow, glass fibers are used in the mat shown in the drawing, rovings or a combination of strands and rovings may be used if desired.

Figure 3:
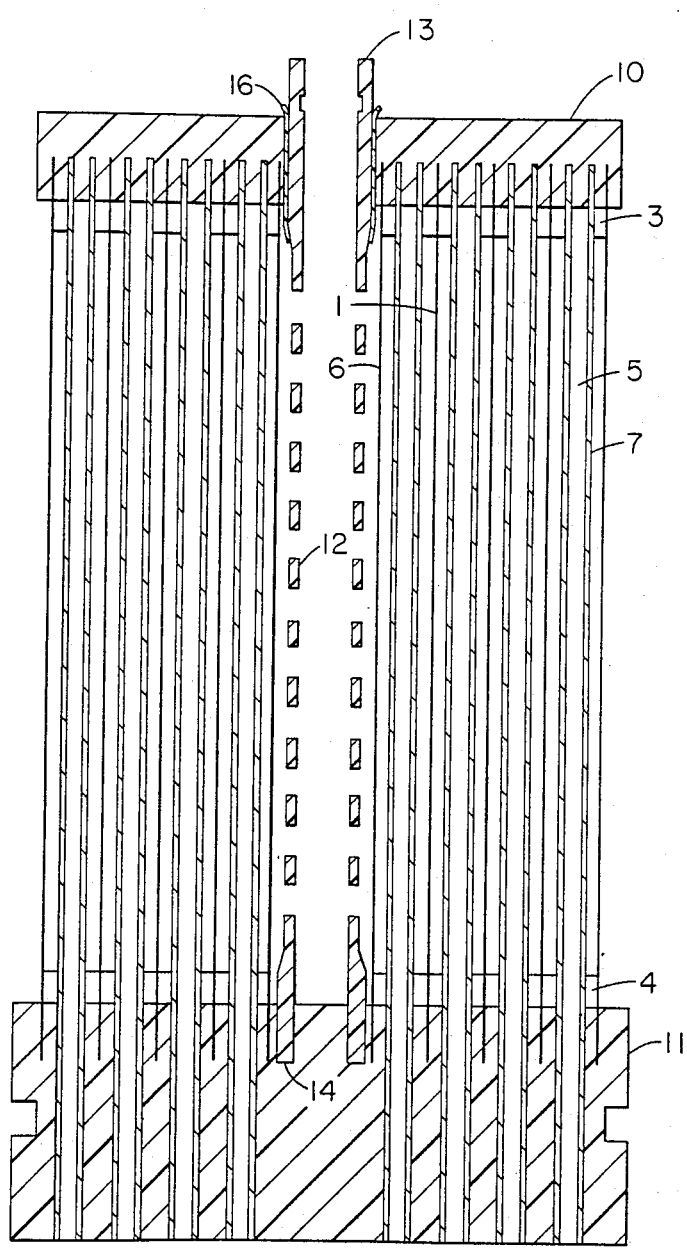
FIG. 3 is a diagrammatic illustration of the mat of FIG. 1 shown used in a cartridge.

In FIG. 1, there is shown a flat, fluid permeable sheet 1 on which are positioned a plurality of hollow glass fiber strands 7 which are fixed to the surface of the permeable sheet 1 and which are in parallel alignment with each other and edges 1c and 1d of the permeable sheet but it will be understood that several layers of strands, 7 are used to form the mat and the strands are placed on top of the single layer shown in FIG. 1 to the desired depth. Extending longitudinally along the permeable sheet 1 and parallel to edges 1a and 1b thereof are two adhesive strips or ribbons 3 and 4. Strips or ribbons 3 and 4 are formed of an adhesive material which is of sufficient depth and width to cohesively bond the strands 7 to one another to keep them in parallel alignment. The strips 3 and 4 also prevent resin wicking during the casting of the mats into cartridges such as shown in FIG. 3. The ribbons 3 and 4 also bond the strands 7 to the permeable sheet 1.

Figure 2:
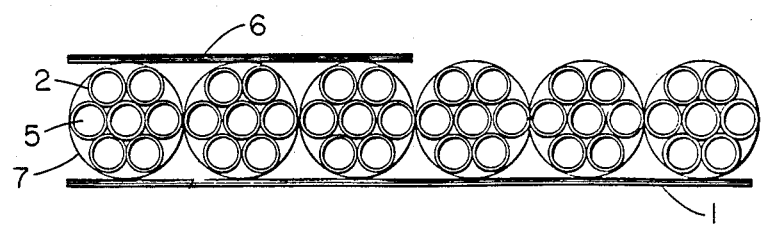
FIG. 2 is a cross-section of the mat of FIG. 1 taken along lines II—II.

FIG. 2 is an enlarged view of a cross-section of FIG. 1 taken along line II—II showing the hollow fibers 2 which make up the strands 7. The fibers 2 as shown have a lumen 5 which runs the length of the fibers 2. As illustrated in the drawing, since strands 7 are employed on the surface of permeable sheet 1, a plurality of hollow fibers 2 (seven in the illustration) are arranged in parallel in each of the strands 7. When additional layers of strands 7 are placed on top of and parallel to the strands 7 shown, a mat having very large numbers of glass fibers is formed. Typically, the strands employed to form the mats contain 100 or more glass fibers. If the fibers used are porous and solid, 200 to 2000 or more filaments may be present. In a hollow fiber mat, the number of fibers in a strand is typically 100 to 160, but can be more. Where rovings are employed, the number of strands making up the roving can be anywhere from 2 to 60, generally 8 to 50. Also shown in FIG. 2 is the inclusion of a second fluid permeable sheet 6, which is of a short width and overlays the first several rows of strands 7 affixed to the permeable membrane 1. The purpose of the permeable sheet 6 is to provide a permeable membrane at one end of the mat so that it can be utilized in a cartridge for use in a filtration or dialysis system through which fluid is introduced through a distributor tube. The sheet 6 protects the first layer of strands from damage by dissipating fluid flow forces entering the mat when it is wrapped around a fluid distributor in a cartridge for example. If desired, the sheet 6 can encompass the entire strand layer. While sheet 6 is shown covering just a single layer of strands, this is for clarity in illustration only. It will be appreciated that sheet 6 typically covers the outside strand layer of multiple layers of strands.

Fluid permeable sheet as used herein is intended to mean any form of structure such as woven or nonwoven mats, cloth, paper and the like, which are pervious to fluid flow through their surfaces, whether the fluid is liquid or gaseous, and which are resistant to attack by the fluid to which they are subjected. Utilization of materials such as fiber glass filament mats, and papers, polyester fiber mats, woven or knitted cloth made of synthetic fibers, glass, cotton and the like can be used. The important consideration for the selection of the material used as the fluid permeable sheet is that it be constructed so that it will support the fibers, strands and rovings to which it is attached and permit free fluid flow through it. The major purpose of the sheet is to protect the fibers, strands and rovings from damage caused by fluid flow forces and by abrasion with each other and surfaces around which the mats of the invention may be wrapped or pressed against in service.

Materials that can be utilized as the ribbons 3 and 4 may consist of hot melt thermoplastic resins or thermoset resins. Some examples of hot melt thermoplastics would be homopolymers or copolymers of polyvinyl acetate, acrylates, acrylonitriles, polysulfones, polyamides and the like. Examples of some thermosets that may be employed are anhydride or amine curable epoxy resins, peroxide curable polyesters, polyimides, and various copolymers of these polymers. These polymers may be dissolved in some solvent and may be contained in a tube with the catalyst. This catalyst can be activated in the presence of heat, oxygen, water or various environments of this nature.

The glass fibers making up the strands and rovings used to prepare the mats range in fiber diameter from 8 microns to about 100 microns, typically 10 to 40 microns. In the case of hollow fibers, the internal diameter of the hollow fibers range between 4 to 90 microns, preferably between 5 and 35 microns.

The hollow fibers in the strands or rovings used to prepare the mat of the instant invention are glass fibers which have been prepared in such a manner that they are provided with a lumen from one end of each of the fibers to the other end so that fluid can flow from one end of a given fiber to the other end of that same fiber unimpeded. A convenient method of preparing hollow fibers is described in assignee's issued U.S. Pat. No. 3,268,313. Particular glass fiber strands that can be used are described in U.S. Pat. No. 3,510,393.

The glass composition forming the fibers used in the strands and rovings used in the mats, as far as the instant invention is concerned, is not of paramount importance and any glass composition suitable for use in making glass fibers which can be drawn into hollow structures as described in the aforesaid U.S. patents is suitable. Typical glasses which may be employed for this purpose are "E" or "621" glasses and/or other borosilicate glasses containing from 8 to 28 percent $B_2O_3$ or more on a weight basis of the glass composition. Glasses of these types are described in U.S. Pat. No. 2,106,744; 2,334,961; 2,571,074; 3,650,721. Glasses having low $B_2O_3$ such as described in U.S. Pat. No. 4,166,747 as well as glasses not containing either fluorine or boron such as described in U.S. Pat. No. 3,847,626 and Applicants' assignee's co-pending application Ser. No. 562,945, filed Dec. 19, 1983 may also be employed.

In those instances, where porous fibers are employed, the porosity is provided to the glass fibers by employing any of many well known techniques to the skilled art. Thus, in treating borosilicate glass fibers, the glass are fibers typically heat treated for a given period of time after which they are treated with a mineral acid to leach out the borosilicate rich phase to provide pores of specific diameter in the fibers. This system is described in Assignees' U.S. Pat. No. 3,630,700 in connection with glass particles, but the systems also apply to treatments involving glass fibers. Assignees' U.S. Pat. No. 3,650,721 shows a system of treating fibers of a boron containing glass which renders them porous using a similar heat treatment followed by an acid leach. Similar treatments to provide porosity to glass fibers are also described in U.S. Pat. No. 4,042,359.

In utilizing the principles described in the above patents for leaching glass fibers, solid or hollow fibers can be treated to provide porosity to the fibers. In the case of hollow fibers, where it is desired, the leaching is normally conducted for a sufficient time to provide pores that communicate with the lumen of the hollow fibers. The treatment of fibers to render them porous can be conducted while the fibers are in fiber, strand or roving form or can be conducted while the strands and rovings are in mat form. It is preferred by Applicants to render fibers porous after they are in mat form and most preferably after they are in a cartridge form such as shown in FIG. 3.

Turning to FIG. 3, an assembly of the mat of FIG. 1 is shown in which the hollow strands 7 are aligned vertically in a cartridge that may be used in a fluid separation system. The cartridge involves an upper casing member 10 in which the strands 7 and the fluid permeable sheets 1 and 6 are cast. The adhesive barrier 3 is located just below the casing member 10. Similarly, the hollow strands 7 are also shown cast in a lower casing member 11 and the adhesive barrier 4 is positioned just above the casing member 11. This barrier 4 serves to prevent wicking of resin into the fibers during the casting of member 11. The lumen 5 shown is for illustrative purposes, it being understood that this represents the lumen of each fiber contained in strands 7. The fluid permeable sheet 6 is wrapped around a distributor tube, generally indicated as 12, that runs in a generally centrally disposed relationship to the hollow strands 7 contained in the cartridge and terminates in the casting 10 forming the top of the cartridge casing. The other end 14 of the distributor tube 12 is embedded in the bottom casing 11. As can be readily seen from the drawing, the first membrane 6 is wrapped completely around the distributor tube 12 and is followed by a layer of hollow strands 2 and then alternate layers of the sheet 1 and the hollow strands 7 as the mat is wrapped in successive wraps around distributor tube 12. A thin plastic sheet 16 is provided around collar 13 at the top of the cartridge.

Figure 4:
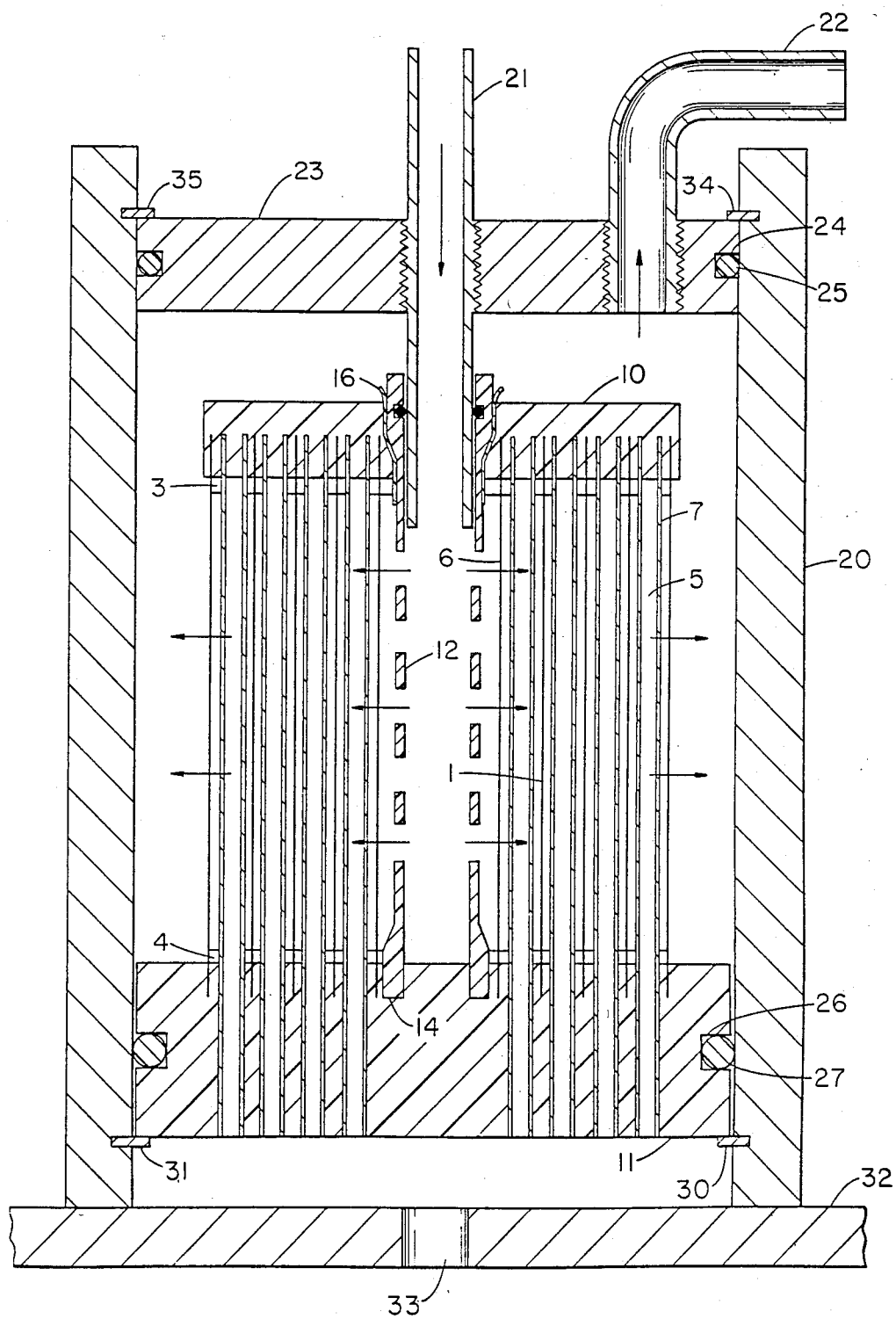
FIG. 4 is a diagrammatic illustration of the cartridge of FIG. 3 in a filtration chamber.

In an operation in which a fluid separation is being conducted, a fluid separation device such as shown in FIG. 4 is utilized. The fluid separation device of FIG. 4 involves a tubular casing 20 which has a fluid inlet 21, a fluid outlet line 22 and a cover member 23 associated therewith. Cover member 23 is sealed with respect to the sidewalls of the casing 20 utilizing grooves 24 and appropriate gasketing 0 rings 25 at the top. On the bottom, the cartridge itself has a groove 26 associated therewith in which is placed an 0 ring 27 to seal the bottom casing of the cartridge to the walls separation unit. In the embodiment shown, the fibers forming the strands 7 are porous as well as being hollow and fluid is fed through inlet 21 into the distributor tube 12 and passes, as shown by the arrows, through the openings 28 in the distributor tube 12 and through the walls of the porous hollow fibers contained in strands 7. The material passing through walls of the fibers contained in strands 7, pass through the lumen 5 of the hollow fibers contained in strands 7 and exits at the end of the resin member 11. The collar 14 of distributor tube 12 is embedded in the member 11 so that fluid entering line 21 must exit through the openings 28 in order to be removed from the system. Fluid that does not pass down through the lumen 5 of the hollow fibers in strands 7 passes to the outside of the cartridge containing the strands 7 and passes between the wall of the casing 20 and the outside of the strands 7 forming the cartridge and upwardly into the feed return duct 22 and out of the system.

In preparing porous glass fibers for use in the mats of the instant invention, recourse to several methods may be had. If the glass fibers, strands or rovings in the mat are made of an "E" or "621" glass composition, the mat may be used in a cartridge such as shown in FIG. 3. In this instance, the cartridge may be placed in a unit such as shown in FIG. 4. The inlet tube 21 is capped and the exit 33 is plugged. The vessel 20 is filled to the cap 10 area with 3 N HCl and maintained in the vessel for 0.5 to 5 hours at 40° to 95° C. The vessel 20 is then emptied, flushed with distilled water and is ready for use. It is an important consideration that the plastic film 16 be present around the collar of distributor tube 12 during leaching the glass strands 7 since they tend to shrink during treatment. This film, which may be thin Mylar ® or other plastic materials such as polyethylene, polypropylene, polyethylene terephthalate, Teflo ® and the like, permits cap 10 to move downwardly as the strands 7 shrink to thereby minimize any fracturing of the strands.

In another method using an "E" or "621" glass composition, the mat is used in cartridge form such as FIG. 3 and placed in a vessel such as FIG. 4. In this method, the mat is leached by passing the leaching acid, typically 3 N HCl, into inlet tube 21 and removing it through outlet 22. In the alternative, the leaching acid can be passed into the vessel through line 22 and removed through line 21. This circulating acid is typically fed for 0.5 to 5 hours at temperatures of 40° to 95° C.

In instances where high boron containing glasses are to be treated, the mats are heat treated to phase separate the glass. This is done by subjecting the mat to temperatures of 200° to 750° C. in an oven for a period of time sufficient to form silica rich and borosilicate rich phases in the glass, typically from 5 minutes to 24 hours. Since the adhesive may not withstand the oven temperatures, it may be necessary to reapply the adhesive ribbons 3 and 4 before leaching the phase separated mat. Preferably, after the mat is phase separated, it is formed into a cartridge such as FIG. 3 and placed in a reactor similar to FIG. 4. Once the mat is in place in a vessel such as FIG. 4, it may then be leached by the methods above described for the "E" and "621" glasses.

In the alternative, the glass fiber strands and rovings can be heat treated before forming them into a mat and subsequently assembled in mat form.

The acids used are typically inorganic mineral acids such as HCl, $H_2SO_4$ and $H_2NO_3$ at normalities of 1 to 6. Strong organic acids such as citric acid may also be used but mineral acids are preferred.

If desired, the mats of "E" or "621" glasses as well as the phase separated borosilicate glasses may be leached by exposing them to the acid treatment in the mat form rather than in cartridge form so long as they are treated for the times and temperatures indicated for the cartridge treatments.

The following is an example of the method used to construct a mat similar to FIG. 1 of hollow glass fibers in roving form.

EXAMPLE

A mat similar to that shown in FIG. 1 was prepared as follows:

Hollow fiber glass strands prepared by the process of U.S. Pat. No. 3,268,313 and contained in a roving package are wound onto a drum. The drum used was manufactured by C. A. Litzler Co. of Cleveland, Ohio. It is 48 inches wide and has a 48 inch diameter. Prior to winding, a clear polypropylene sheet is taped to the drum surface. This prevents the adhesive, which is applied later, from sticking to the winder. A 10 mil, fluid permeable, polyester surface mat (Dupont's Reemay ®) mat is taped to the drum winder, over the polypropylene sheet. The porous polyester mat forms the support backing for the yet to be wound glass roving. A roving containing E-glass fibers with 2% epoxy sizing on the fibers is used to supply fibers for a mat. The roving consists of 40 strands, each strand containing 102 individual hollow fibers whose dimensions are approximately 12 microns O.D. and 6 microns I.D.

The roving is wound onto the drum and results in 14 rovings per inch, or 560 strands per inch or 57,120 fibers per inch. The roving is continuously wound onto the drum with the rovings generally parallel to each other until the drum is covered. The mat resulting is measured and marked at 13 inch sections on the drum. Each mat section will come from the 13 inch×44 inch pieces (2 inches are lost at each end of the drum). Prior to cutting the mat and removing it from the drum, the adhesive strips 3 and 4 are applied. In this instance, a contact cement manufactured by Franklin Chemical of Columbus, Ohio is used.

Two ½ inch adhesive lines are applied to each mat section. One line is one inch from the end, the other is 2½ inches from the other end. The adhesive lines run perpendicular to the fiber direction and serve to both bond the fibers together and to the polyester fluid permeable sheet as well as serving later to prevent resin wicking during casting of the ends. Once the adhesive has dried, the blanket is cut at one of the mat locations. This permits removal of the blanket from the drum winder. The blanket is laid onto a cutting table, and a 13 inch×22 inch hollow fiber mat is cut. Using this procedure, a mat is provided which, when used in a 2" diameter module or cartridge such as shown in FIG. 3 has available for use in that cartridge, 370,480 hollow fibers.

As will be readily appreciated, the mats of the instant invention provide a source of hollow fibers or hollow porous fibers or porous fibers in a mat form which, can be made to accommodate in a small area extremely large quantities of these fibers for use in commercial filtration and immobilization reactors. In instances where cartridges of layer dimensions are employed, it will be appreciated that vast amounts of fibers will be present. For example, in a 4" diameter module, it would typically require the use of mats that would provide typically 2,227,000 fibers.

While the invention has been described with reference to certain specific embodiments and illustrative examples, it is not intended to be limited thereby, except insofar as appears in the accompanying claims.

We claim:

1. A glass fiber containing composite mat having a plurality of glass fiber strands affixed to a fluid permeable sheet, said strands being present in layers and oriented generally parallel to each other, the fibers of the glass fiber strands being between 8 and 100 microns in diameter and having pores provided in them, at least two strips of an adhesive spaced from each other and inboard of the ends of said glass fiber strands, said adhesive affixing the glass fiber strands to said sheet and to each other throughout the layers to thereby form an integral, composite mat.

2. The composite mat of claim 1, wherein a second permeable sheet is placed on top of several rows of said glass fiber strands at one end of said mat.

3. The mat of claim 1 wherein the glass fibers as "E-glass" fibers.

4. The composite mat of claim 1, wherein the fibers in said strands are also provided with a lumen throughout their length.

5. The mat of claim 4 wherein a second permeable sheet is placed over several rows of said strand at one end of said mat.

6. The mat of claim 4 wherein the glass fibers are "E-glass" fibers.

7. A glass fiber containing composite mat having a plurality of glass fiber rovings affixed to a fluid permeable sheet, said rovings being generally parallel to each other and the glass fibers in said rovings having pores in them, at least two strips of an adhesive spaced from each other and inboard of the ends of said rovings, said adhesive affixing the rovings to said sheet and to each other to thereby form an integral, composite mat.

8. The composite mat of claim 7, wherein a second permeable sheet is placed on top of several rows of said rovings at one end of said mat.

9. The mat of claim 7 wherein the glass fibers as "E-glass" fibers.

10. The composite mat of claim 7 wherein the fibers in said rovings are also provided with a lumen throughout their length.

11. The composite mat of claim 10 wherein a second permeable sheet is placed on top of several rows of said rovings at one end of said mat.

12. The mat of claim 10 wherein the glass fibers are "E-glass" fibers.

13. A fiber glass containing mat composite comprising a first permeable sheet having two major surfaces and four edge surfaces, a plurality of parallel aligned porous glass fiber strands in contact with one of the major surfaces of said sheet with their ends facing two opposing edges of the sheet and plied in layers on top of each other, a ribbon of adhesive spaced inwardly of said two opposing edges, said adhesive ribbon being of sufficient width and depth to thereby affix said porous glass fiber strands to each other and to said first permeable sheet to maintain said strands in alignment with each other, said ribbons being generally parallel to each other and said two opposing edges and thereby forming a composite mat.

14. The mat of claim 13 wherein a second permeable sheet is placed on top of several rows of said glass fiber strands and associated ribbon of adhesive at one end of said mat.

15. The mat of claim 13 wherein the glass fibers are "E-glass" fibers.

16. The mat of claim 13 wherein the glass fibers in said glass fiber strands are hollow along the long axis thereof.

17. The mat of claim 16 wherein a second permeable sheet is placed on top of several rows of said glass fiber strands and associated ribbon of adhesive at one end of said mat.

18. The mat of claim 16, wherein the glass fibers are "E-glass" fibers.

19. A fiber glass containing mat composite comprising a first permeable sheet having two major surfaces and four edge surfaces, a plurality of parallel aligned porous glass fiber rovings in contact with one of the major surfaces of said sheet with their ends facing two opposing edges of the sheet, a ribbon of adhesive spaced inwardly of said two opposing edges, said adhesive ribbon being of sufficient width and depth to thereby affix said rovings to each other and to said first permeable sheet and maintain said rovings in alignment with each other, said ribbons being generally parallel to each other and said two opposing edges and thereby forming a composite mat.

20. The mat of claim 19, wherein a second permeable sheet is placed on top of several rows of said porous glass fiber rovings and associated ribbon of adhesive at one end of said mat.

21. The mat of claim 19 wherein the glass fibers are "E-glass" fibers.

22. The mat of claim 19 wherein the glass fibers in said porous glass fiber rovings are also hollow along the long axis thereof.

23. The mat of claim 22 wherein a second permeable sheet is placed on top of several rows of said rovings and associated ribbon of adhesive at one end of said mat.

24. The mat of claim 22, wherein the glass fibers are "E-glass" fibers.

* * * * *